(12) United States Patent
Mirabella

(10) Patent No.: US 9,308,111 B1
(45) Date of Patent: Apr. 12, 2016

(54) ORTHOPEDIC BRACE AND METHOD OF USE

(71) Applicant: Andrew D. Mirabella, Medina, OH (US)

(72) Inventor: Andrew D. Mirabella, Medina, OH (US)

( * ) Notice: Subject to any disclaimer, the term of this patent is extended or adjusted under 35 U.S.C. 154(b) by 0 days.

(21) Appl. No.: 14/690,294

(22) Filed: Apr. 17, 2015

(51) Int. Cl.
  *A61F 5/00* (2006.01)
  *A61F 5/01* (2006.01)

(52) U.S. Cl.
  CPC .................................... *A61F 5/0127* (2013.01)

(58) Field of Classification Search
  CPC .............. A61B 18/1445; A61B 2017/00398; A61B 2017/00544; A61B 17/064; A61B 17/068; A61B 17/0686; A61B 17/072; A61B 17/07207; A61B 17/105; A61B 17/115; A61B 17/1222; A61B 2017/07271; A61B 17/00491; A61B 17/0057; A61B 17/12022; A61B 17/12118; A61B 17/12181; A61B 17/3468; A61B 18/02; A61B 18/04; A61B 18/1492; A61B 18/18; A61B 18/245; A61B 2017/00411; A61B 2017/005; A61F 2/2445; A61F 2/06; A61F 2/2442; A61F 5/003; A61F 2210/0014; A61F 2220/0016; A61F 2230/0069; A61F 2/243; A61F 2/2466; A61F 5/0102; A61F 5/026; A61F 5/028; A61F 13/2002; A61F 5/0109; A61F 5/05841; A61F 5/0118; A61F 5/0193; A61F 13/04; A61F 5/0111; A61F 5/05825; A61F 5/0585; A61F 13/069; A61F 13/08; A61F 2013/00093; A47D 13/025; A47D 11/00; A47D 13/02; A47D 13/046; A47D 13/086; A47D 15/00; A47D 1/103; A47D 9/00; A61N 2005/1087; A61N 5/1077; A61N 5/1039; A63B 21/0552; A63B 21/0557; A63B 21/1449; A63B 21/1469; A63B 2209/10; A63B 21/0442; A63B 21/1426; A63B 23/03541; A63B 21/00065; A63B 21/1434; A63B 2210/50; A63B 23/03575; A63B 21/04; A63B 21/0421
  USPC ........................ 128/878–879, 882; 602/20–28
  See application file for complete search history.

(56) References Cited

U.S. PATENT DOCUMENTS 3,935,858 A * 2/1976 Harroff ................. A61F 5/0585
    602/26
4,753,229 A  6/1988 Sutherland
(Continued)

*Primary Examiner* — Michael Brown
(74) *Attorney, Agent, or Firm* — John F. Rollins

(57) ABSTRACT

An orthopedic brace may include a main panel made of a flexible, breathable elastic fabric, such as perforated neoprene or AIRPRENE.® The main body panel includes a a fastening implement, such as hook-and-loop fasteners to secure the main body panel in an encircling position on or near a subject area of the human body. The brace may a shank embedded in the main panel to add rigidity in one or more areas. At least two adjustable strap loops may cooperate with the shank to provide targeted and precise compressive forces to the treatment area when the brace is installed. The strap loops may be anchored at one end to the main panel, extend through sliding rings and may be provided with fasteners at another end to adjustably engage corresponding fastening pads on the main body panel. The adjustable strap loops, rings and shank cooperate to provide for the targeted and precise application and distribution of pressure force to the treatment area.

20 Claims, 6 Drawing Sheets

(56) References Cited

U.S. PATENT DOCUMENTS

| | | |
|---|---|---|
| 5,088,478 A | 2/1992 | Grim |
| 5,139,477 A * | 8/1992 | Peters ............... A61F 5/0106 602/23 |
| 5,395,399 A * | 3/1995 | Rosenwald ........ A61F 5/0104 607/108 |
| 5,415,624 A * | 5/1995 | Williams ........... A61F 5/0104 602/14 |
| 5,620,413 A | 4/1997 | Olson |
| 5,860,423 A | 1/1999 | Thompson |
| 5,891,073 A | 4/1999 | Deirmendjian |
| 6,080,121 A * | 6/2000 | Madow ............... A61F 5/0109 128/876 |
| 6,450,131 B1 * | 9/2002 | Broman .............. A61F 5/026 119/857 |
| 6,617,485 B2 | 9/2003 | Herzberg |
| 6,656,098 B2 | 12/2003 | Hoffman |
| 6,929,617 B2 | 8/2005 | McCormick et al. |
| 7,267,656 B2 | 9/2007 | Cooper |
| 7,753,865 B1 | 7/2010 | Hely |
| 8,202,239 B2 | 6/2012 | Wilkerson |
| 2006/0206045 A1 * | 9/2006 | Townsend .......... A61F 5/0125 602/26 |
| 2011/0028877 A1 | 2/2011 | Vollbrecht et al. |

\* cited by examiner

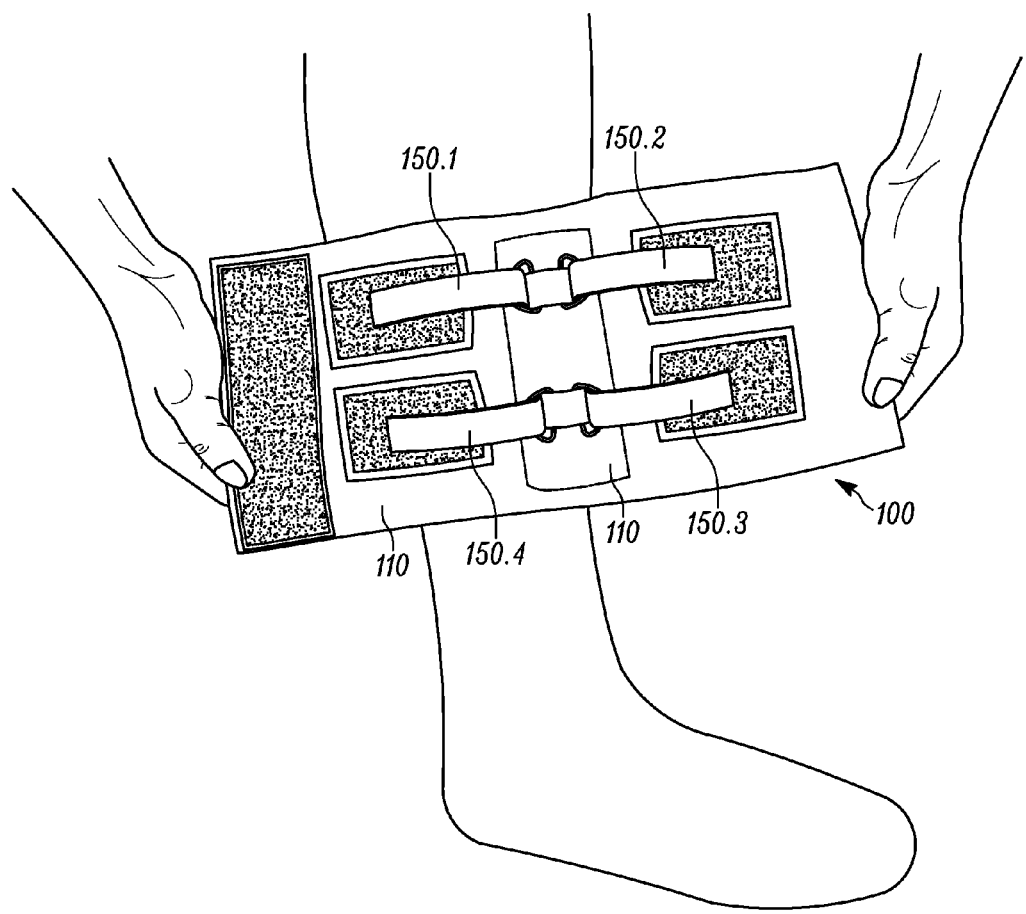
FIG. 4.1

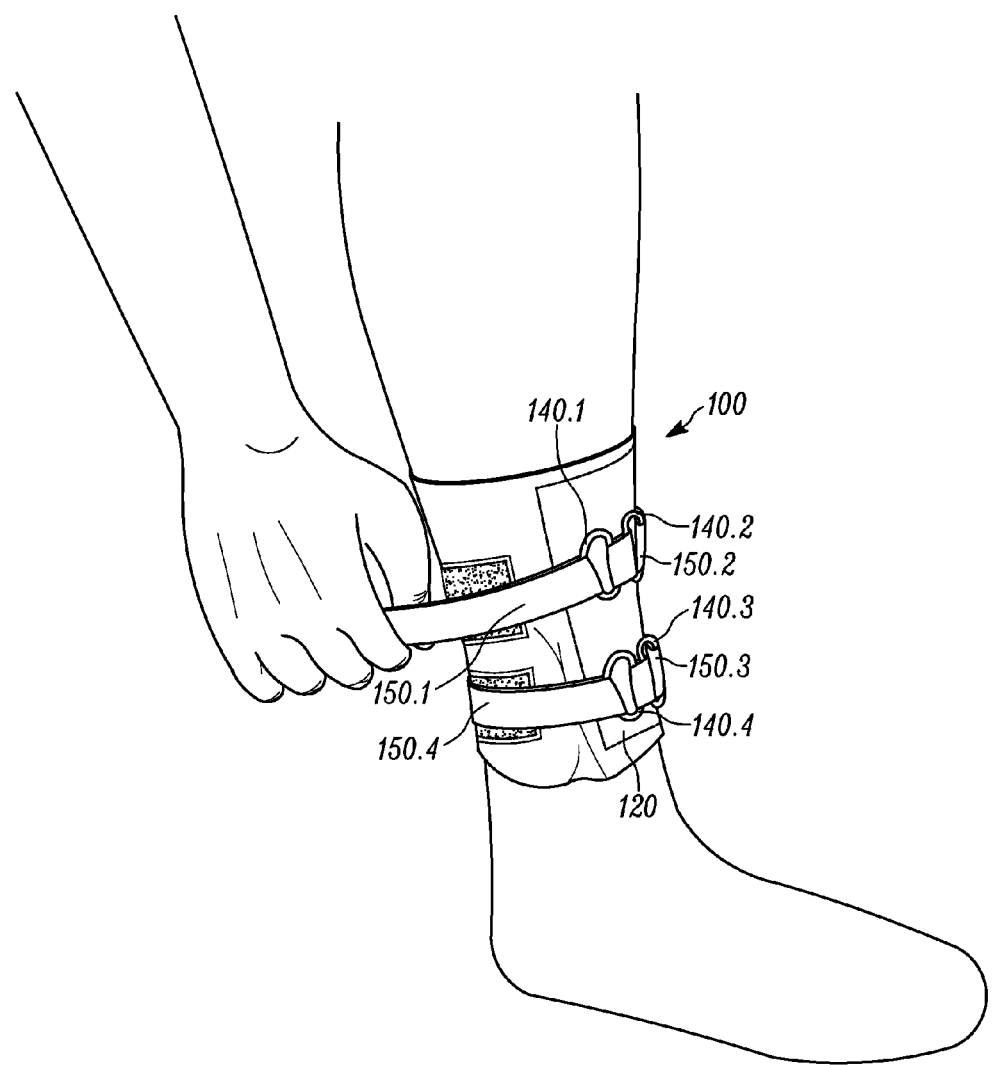
FIG. 4.2

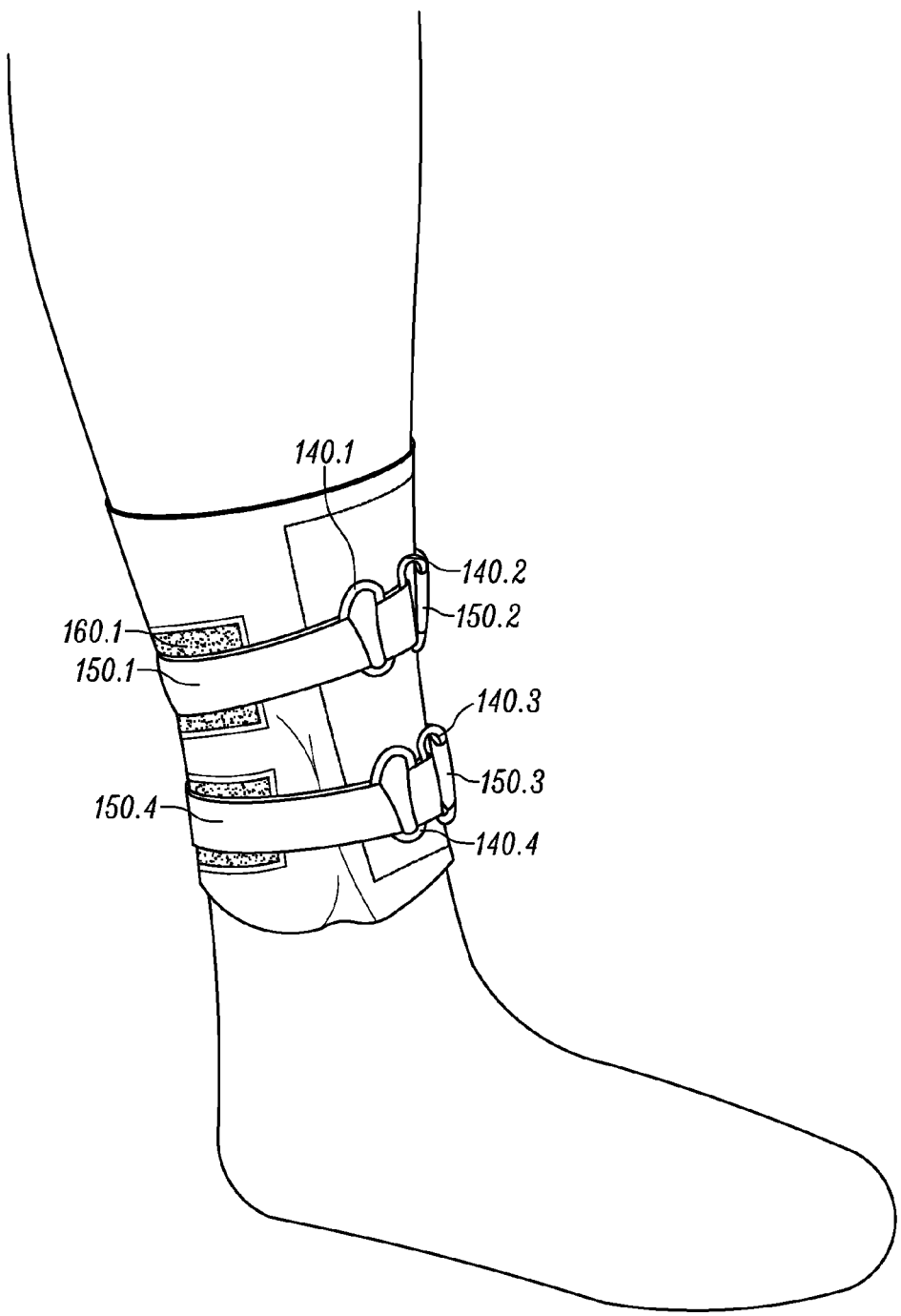
FIG. 4.3

ORTHOPEDIC BRACE AND METHOD OF USE

BACKGROUND

1. Technical Field

The disclosure relates to orthopedic braces for stabilizing and/or protecting and preventing injury to an area of interest, such as an injured ankle, on a human subject.

2. Prior Art

Various brace and ankle brace configurations are known in the prior art for the treatment of injuries, such as lateral ankle sprains, which are the most common form of ankle injury experienced by athletes and others. Such device are typified by U.S. Pat. Nos. 8,202,249; 7,753,865 and 7,267,656, for example.

New research is indicating that traditional treatments for injuries, such as ankle injuries, involving rest/idleness of the joint as well as thermal (ice) therapy may not be as effective as mobilization and movement of the joint and pumping action of the associated muscles immediately following injury. See for example, http://guardianlv.com/2014/04/ice-age-melting-rice-may-no-longer-be-the-treatment-of-choice-for-injuries. As a result, physiotherapists are more frequently employing the use manipulative therapy techniques to treat dysfunction and pain resulting from ankle sprains and other injuries. A form of therapy known as "Mulligan's Mobilization with Movement" treatment (MWM) has been known for the treatment of acute ankle pain following a plantar flexion/inversion injury. See "A study of the effects of Mulligan's mobilization with movement treatment of lateral ankle pain using a case study design," Manual Therapy (1998), 3(2), 78-74, Harcourt Brace & Co., Ltd. See also, Mulligan, Brian R., "Manual Therapy" $3^{rd}$ Edition, Planeview Service, Ltd. Wellington, New Zealand, 1995. The technique is a manual technique that involves a physiotherapist sustaining a posterior glide to the distal fibula while the patient actively inverts the ankle several times. In physiotherapy, a "glide" involves the application of manual pressure by the therapist to a muscle, muscle group or human body area of interest, combined with sliding movement of the therapist's hands or fingers along path that coincides with area to be treated. In the case of treatment for ankle sprains, the MWM technique may involve the application of a sustained anterior posterior cranial glide of the lateral malleolus on the tibia. With the glide maintained, the patient then performs active movement of the injured joint with therapist providing overpressure at an end range of motion. Following the MWM, the glide is typically maintained with a specific tape application applied in the direction of the MWM to help maintain the corrected position of the fibula.

Challenges in the relevant art include providing brace devices that take advantage of these relatively new injury treatment techniques and principles, while providing brace structures that provide sufficient support to the area of interest and that still permit flexibility and a range of motion, such that an athlete, for example, could re-engage in activities promptly following an injury.

Yet another challenge in the art is to provide brace configurations that are easy to deploy (install) and remove, and which do not require the attention of a person besides the user for adjustment and or installation/removal.

Yet another challenge is to provide orthopedic braces that may provide therapeutic effects, such as MWM or like effects, to the area of interest while being worn by a human subject.

There is thus a need in the art for brace devices and associated methods that address these challenges. The subject matter of the present disclosure is directed to overcoming, or at least reducing the effects of, one or more of the problems of the prior art set forth above, and others.

SUMMARY OF THE INVENTION

According to one aspect, the brace may include a main panel comprised of a flexible, breathable elastic fabric, such as perforated neoprene or AIRPRENE.® The main body panel may be provided with a fastening implement, such as hook-and-loop fasteners to secure the main body panel in an encircling position on or near a subject area of the human body. The brace may include at least one rigid or semi-rigid member or shank embedded or otherwise cooperatively associated with the main panel to add rigidity in one or more areas. At least two adjustable strap loops may cooperate with the shank to provide targeted and precise compressive forces to the treatment area when the brace is installed. The strap loops may be anchored at one end to the main panel, extend through sliding rings and may be provided with fasteners at another end to adjustably engage corresponding fastening pads on the main body panel. The adjustable strap loops, rings and shank cooperate to provide for the targeted and precise application and distribution of pressure force to the treatment area.

The orthopedic braces according to aspects of the invention may thus provide an adjustable and ideal constant pressure to a treatment area, which may result in pain relief to the human subject. In the case of an ankle brace, for example, the shank position and strap loops length may be selected to implement pressure therapies that are consistent with the MWM methods, such as providing for constant and optimal pressure in in an area of the leg just above the ankle while the brace is being worn, resulting in immediate pain relief and increased range of motion to the human subject even immediately following ankle sprain.

According to another aspect, the strap loop adjustment system and particular orientation of the adjustment straps and nature of the fasteners provides for quick and easy installation, removal and adjustment and allows the human subject to deploy the brace to the treatment area and to adjust the brace pressure without assistance from another person.

According to another aspect of the invention, an orthopedic brace may be used preventatively and may provide improved support to the treatment areas in order to protect the treatment area and to prevent injury, such as an ankle sprain.

According to another aspect, a method of using an orthopedic brace for ankle sprain treatment may involve the steps of wrapping the brace around the lower leg, just above the ankle joint, and fastening the main panel fastener such that the main panel is in a snug, encircling position with the shank member oriented in the middle of the lower leg and in a lateral anterior position; pulling the brace upward on the leg to further tighten the brace; rotating the brace towards the outside of the leg so that the shank is just lateral of the middle lower leg and positioned to press against the outside leg muscle but not on the shin; and tightening the strap loops to provide a desired supportive compressive force of the shank on the muscles of the outside lower leg.

DESCRIPTION OF THE DRAWINGS

The above and other attendant advantages and features of the invention will be apparent from the following detailed description together with the accompanying drawings, in which like reference numerals represent like elements throughout. It will be understood that the description and embodiments are intended as illustrative examples and are not intended to be limiting to the scope of invention, which is set forth in the claims appended hereto.

FIGS. 4.1, 4.2 and 4.3 illustrate a method of installing an orthopedic brace according to an aspect of the invention.

DETAILED DESCRIPTION

Figure 1:
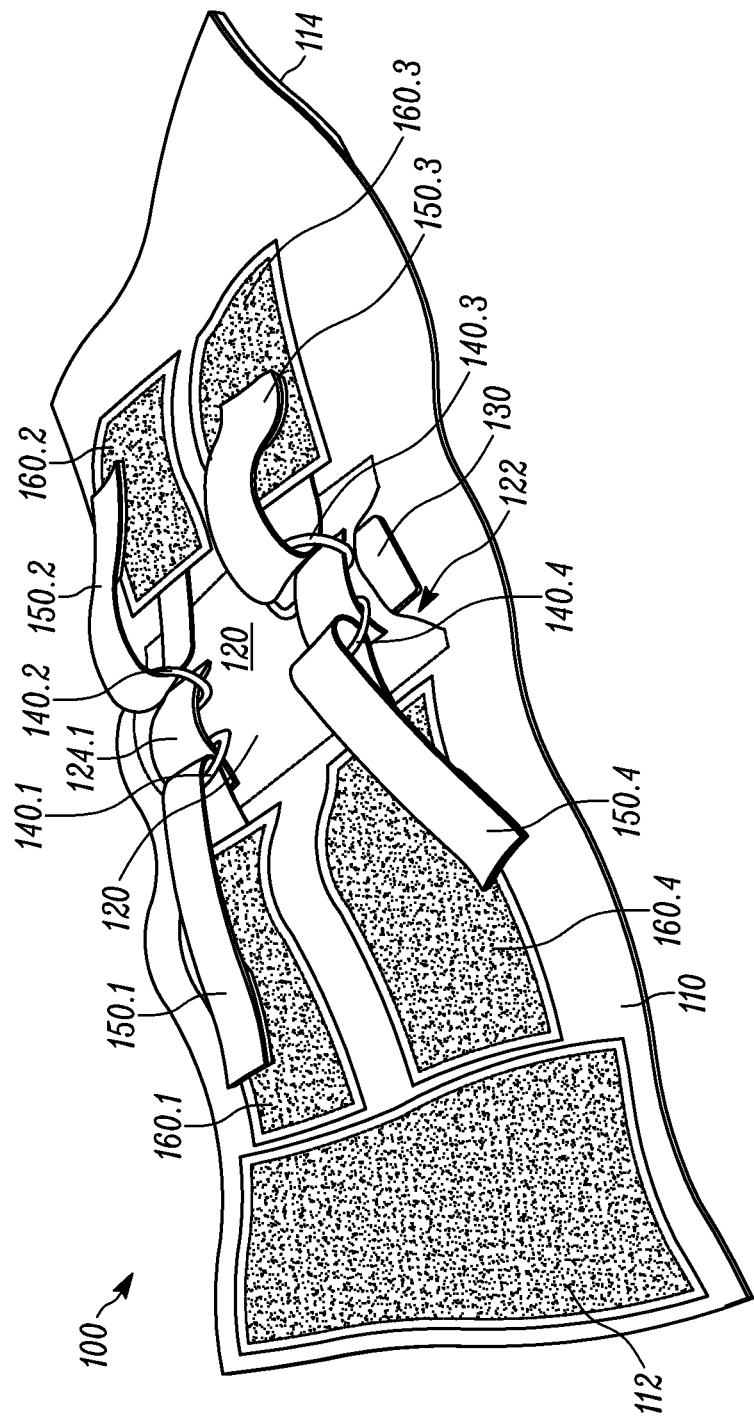
FIG. 1 is a perspective showing a four-strap orthopedic brace configuration according to an aspect of the invention.

FIG. 1 is a perspective view of an ankle brace 100 according to an aspect of the invention. A generally rectangular, flexible main body panel 110 may be constructed of neoprene, AIRPRENE,® nylon or any other suitable fabric or a combination thereof and may include cooperating fasteners 112 and 114, which may comprise hook-and-loop type fasteners such as VELCRO,® or other fasteners for securing the main body panel in an encircling position on a human leg or ankle. Alternate fasteners may be used, such as buttons, clasps or other releasable, non-permanent fastening devices or materials. Main body panel 110 may also be provided with a shank retaining panel 120, fastened thereto by stitching or other fastening implements, and which forms a pocket 122 with the main body panel for retaining a rigid or semi-rigid shank or reinforcing member 130 therein. The shank or reinforcing member 130 may be constructed of metal, such as aluminum, plastic, such as Ultra High Molecular Weight (UHMW) thermplastic, such as polyethylene, or other suitable material that provides a desired rigidity (elastic modulus) to achieve structural support and transfer and distribution of forces to the treatment area The reinforcing member or shank 130 may have some degree flexibility for comfort to the user during activity. Moreover, although the example shank or reinforcing member 130 described herein is generally rectangular in shape, it may be shaped differently, such as a rod or member having a circular, elliptical or other cross-section. Moreover, the reinforcing member or shank 130 may be provided as a contoured plastic piece that is custom made for a particular user. As will be appreciated, the brace configuration, including the pocket or other implement for removably securing the reinforcing member to the main panel permits the use of differently shaped reinforcing members, which may be interchanged with a given brace, depending on application, user and other variables. A position indicator may be provided on the brace, such as line or other indicia on the shank-retaining panel 120 to indicate a precise position of a centerline or axis of the shank when the main panel is installed so that the forces applied to the treatment area can be applied precisely by the wearer.

The shank retaining panel 120 may include one or more ring anchoring panels 124.1 and 124.2 for anchoring strap rings 140.1, 140.2, 140.3 and 140.4 to a central portion of the main body panel, which central portion coincides with the shank 130 such that tension forces on the rings 140 may be transmitted to the shank 130.

Respective straps 150.1, 150.2, 150.3 and 150.4 cooperate with the rings 140.1, 140.2, 140.3 and 140.4 to provide for tightening compressive forces on the main body panel 110 and on the subject area of the human body. An anchored end 152.1, 152.2, 152.3 and 152.4 of each strap is attached via stitching or other fastening implement to the main body panel at respective attachment locations. A fastening end 154.1, 154.2 154.3 and 154.4 of each strap may be provided with a hook-type fastening fabric and selectively positioned and fastened to a loop type fastening pad 160.1, 160.2 160.3 and 160.4, each secured to the main body panel 110 at an appropriate position. In this manner, compressive forces may be adjustably applied to the ankle brace when installed in an encircling position on a human subject.

Figure 2:
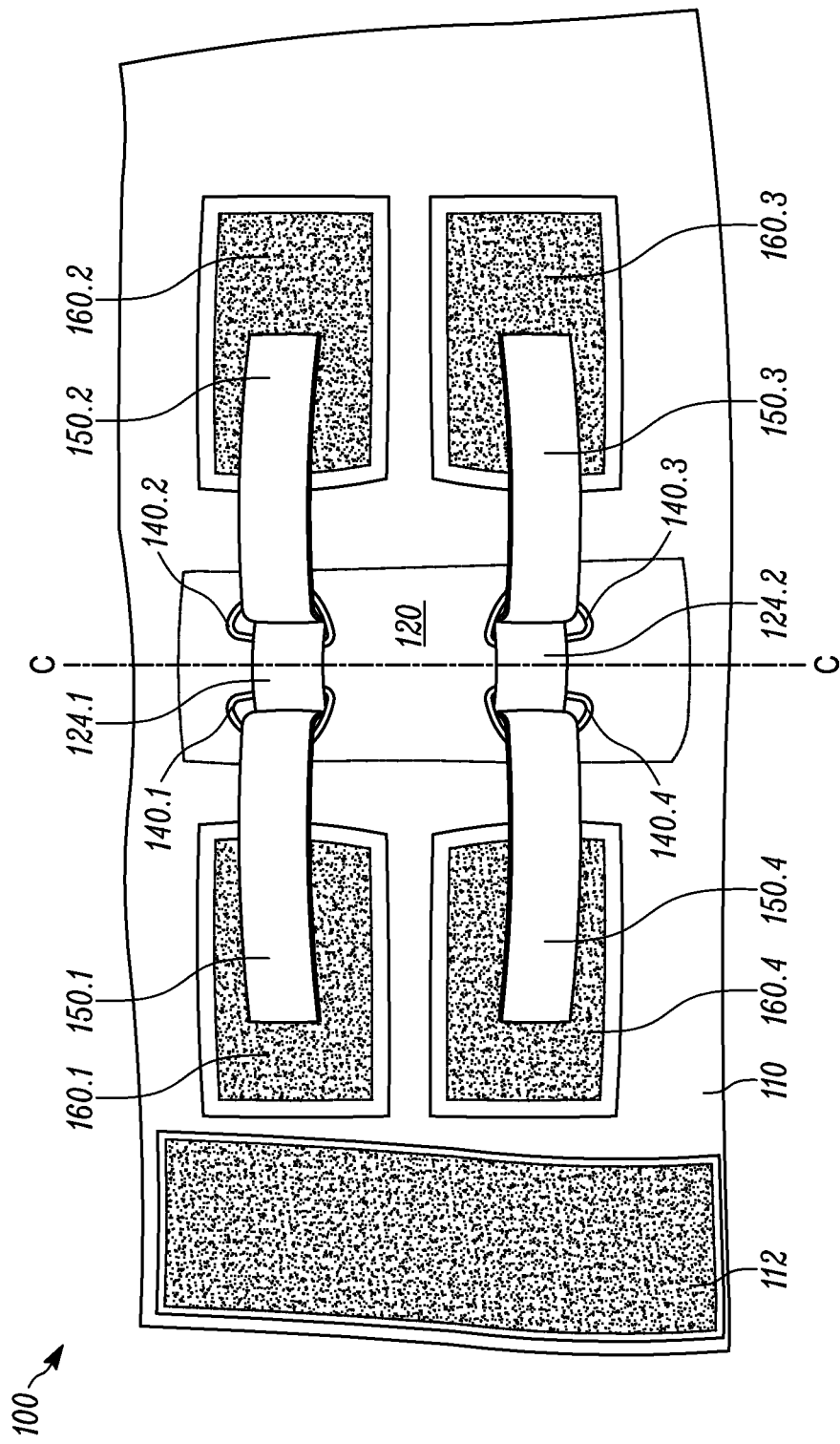
FIG. 2 is a top, plan view of the brace of FIG. 1.

As will be appreciated, the example described in FIG. 1 is a four-strap system, with two upper and two lower straps that provide for four-way adjustment of the compressive forces on the ankle brace. The spacing of the fastening pads 160 from a central plane or axis (C-C in FIG. 2) coinciding with the shank, as well as the length of straps 152, may be selected to provide for the appropriate positioning of the fastening pads, and corresponding application of compressive forces by the shank, straps and brace as a whole, in desired areas related to the subject human body area to be treated or protected. For example, the fastening pad position and and strap length may be selected such that forces are applied at a position that is substantially opposite or diametrically opposed to the shank 130 when the brace is installed in an encircling position. In other words, the fastening ends straps 150 may be sized and adapted to be fastened to an area on the main body panel 110 such that pressure forces may be directed to a desired area while the brace is being worn. Moreover, owing to the interaction of the straps, rings, shank and main body panel, therapeutic effects and improved support and flexibility are provided to the human subject.

Figure 3:
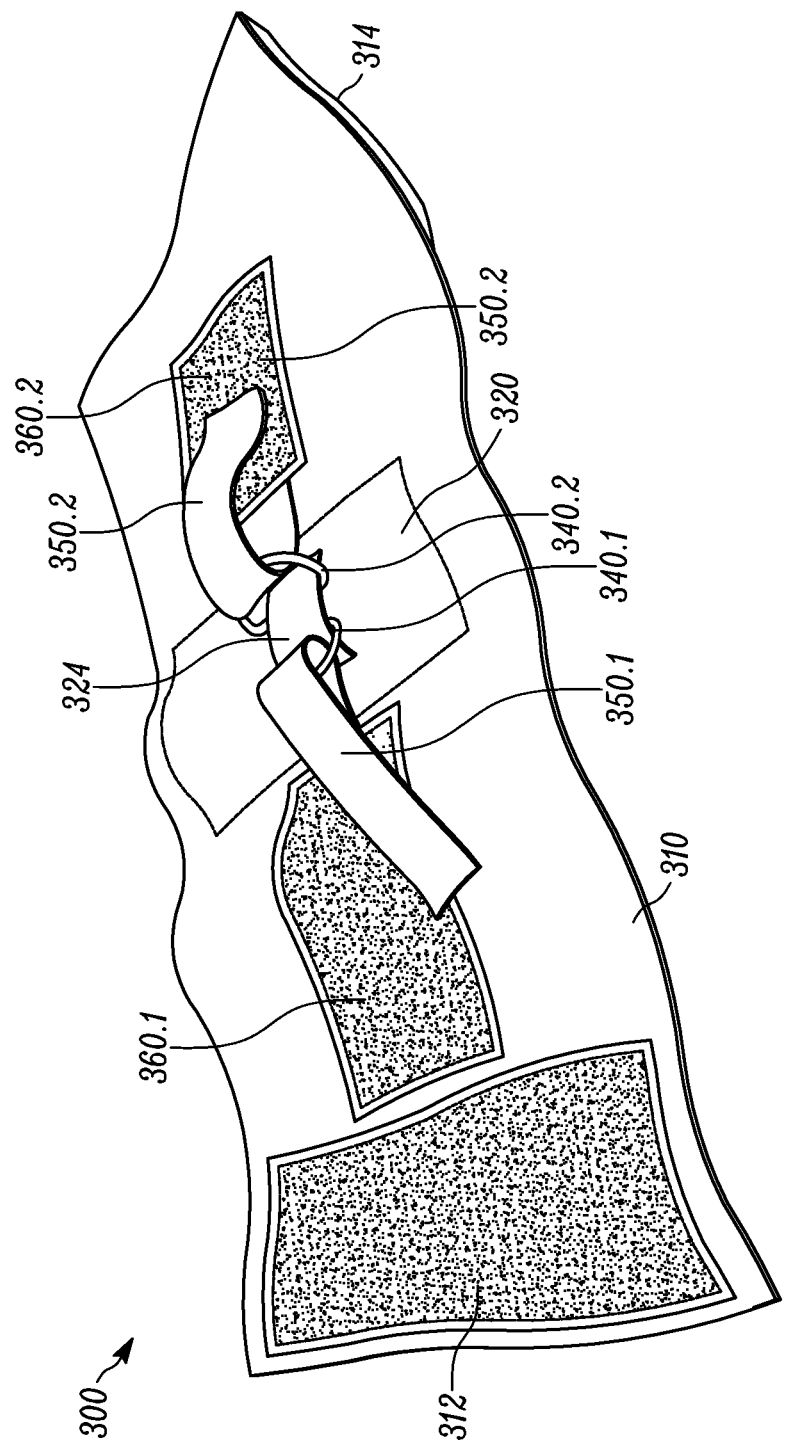
FIG. 3 is a perspective showing a second orthopedic brace configuration having two straps according to an aspect of the invention.

FIG. 3 illustrates a two-strap brace 300 according to another aspect of the invention. Main body panel 310 is provided with fasteners 312 and 314, which may secure the brace in an encircling position on the human subject. A shank (not shown in FIG. 3) is secured within a shank-retaining panel 320, secured to the main body panel 310. A ring-anchoring panel 322 secures two D-rings, 340.1 and 340.2 therein, each cooperating with respective straps 350.1 and 350.2 to provide tension to the brace 300 and to provide compressive forces on the shank and one or more areas of the human subject where pressure is desired.

Sliding rings may be a standard metal "D" ring as is known in the art. Alternatively, plastic rings, buckles or sliding and/or gripping fasteners, such as plastic rings sold under the name "Triglide" by WBC Industries, Inc., Part Number PL103A-16BK, or other known fasteners used in orthotics or prosthetics may be utilized in place the example metal D-rings described in reference to the Figures. In addition, a buckle-type fastening implement secured near the shank may be used in place of the hook and loop fastening pads. It will be recognized that any implement which provides for the adjustment and maintaining of compressive forces on the shank of the main panel will be suitable for achieving one or more aspects of the invention.

FIGS. 4.1, 4.2 and 4.3 illustrate a four-strap brace, such as that described above in relation to FIGS. 1 and 2, and an associated method of using an orthopedic brace. In FIG. 4.1, a user is shown installing the brace on an area of interest on the human body, namely an area above the ankle for application of pressure in targeted locations to achieve a desired therapy, such as MWM. According to an aspect of the invention, the method may involve treatment of ankle sprains by installing the brace in an area above the ankle on the human leg, as shown. Initial installation begins with the step of wrapping the brace 100 around an area of the lower leg, just above the ankle joint, and fastening fasteners 112 and 114 together for a snug fit. The orientation of the shank (hidden by shank retaining panel 120) is in the front middle of the lower leg. Next, the brace may be pulled in an upward direction towards the knee by about an inch to provide for increased tightening. Next, referring additionally to FIG. 4.2, the brace may be rotated slightly in a clockwise direction looking down at the foot, such that the shank is rotated to a position that is just to the right of the middle of the lower leg and pressing against the outside leg muscle (tibialis anterior), just adjacent to the shin bone. The strap loops 150 are adjusted and fastened to provide a desired force on the shank as shown in FIG. 4.2. And the brace is in an installed position shown in FIG. 4.3.

According to an aspect of the invention, the brace may be provided with other therapeutic measures. For example, moist heat or cooling therapy materials may be incorporated into the main panel for providing thermal therapy to the body area. Such materials may be contained in separate bags or containers and housed in pockets on the brace so as to provide for insertion and removal of the bags without requiring removal of the brace. Similarly, medicament therapies, such as menthol sources or other chemical therapies may be provided.

It should be understood that implementation of other variations and modifications of the invention in its various aspects may be readily apparent to those of ordinary skill in the art, and that the invention is not limited by the specific embodiments described herein. It is therefore contemplated to cover, by the present invention any and all modifications, variations or equivalents. For example, air cushions, gels, shock absorbing materials, or heat or moisture therapy materials including microwavable heat and moisture absorbing materials, may be provide as part of the device for additional therapeutic and healing effects.

What is claimed is:

1. An orthopedic brace for bracing and protecting a treatment area of a human body comprising:
    a) a flexible main panel for encircling the treatment area, the main panel having a main panel fastener for securing the main panel in an encircling position around the treatment area;
    b) at least one reinforcing member cooperating with the main panel to transmit force to the treatment area and being disposed in a central area of the main panel;
    c) at least two straps, each secured at one respective end to the main body panel;
    d) a pair of sliding rings, at least one respective sliding ring associated with each of the at least two straps and secured in the central area of the main panel for permitting sliding movement of the at least one strap therethrough, wherein the pair of sliding rings are secured by a ring-anchoring panel extending across the at least one reinforcing member;
    e) at least one respective strap fastener for securing a fastening end of each of the at least two straps to the main panel, wherein the straps are adapted to extend through a respective one of the sliding rings and double back around the main panel to provide compressive forces on the reinforcing member via the sliding rings, wherein the at least two straps, sliding rings and reinforcing member cooperate to provide targeted forces to the treatment area.

2. The brace of claim 1, wherein the at least two straps comprises four straps.

3. The brace of claim 1, wherein the sliding rings are metal D-rings.

4. The brace of claim 1, wherein the reinforcing member is embedded in a pocket formed on the main body.

5. The brace of claim 1, wherein the reinforcing member is a semi-rigid member.

6. The brace of claim 1, wherein the main panel is shaped to surround a treatment area above the human ankle and where the location of the reinforcing member relative to the main panel, and the length of the least two straps are such that the brace, when deployed to the treatment area, applies pressure through the reinforcing member to an anterior location on the leg above the ankle, and to a posterior area of the leg above the ankle.

7. The brace of claim 1, further comprising a reinforcing member position indicator for indicating the position of the reinforcing member relative to the treatment area when the brace is in an encircling position.

8. The brace of claim 1, wherein the reinforcing member comprises metal.

9. The brace of claim 1, wherein the anchoring panel includes opposed ends secured to the main panel and slidably secures the pair of sliding rings for limited lateral movement relative to the main panel.

10. The brace of claim 1, further comprising an anchoring panel having ends secured to the main panel and slidably securing the pair of sliding rings to a central portion of the main panel wherein the anchoring panel extends across the reinforcing member such that when tension is applied to the straps, the sliding rings apply forces to the reinforcing member.

11. The brace of claim 1, wherein the main panel comprises a breathable, elastic fabric.

12. The brace of claim 1, where in the main panel comprises AIRPRENE.

13. The brace of claim 1, where the main panel fastener and the strap end fasteners comprise the hook or loop fastener portion of a hook-and-loop fastener.

14. The brace of claim 1, wherein the main panel is dimensioned to encircle and provide support to the area of the human leg above the ankle to treat an ankle sprain.

15. A method of using an orthopedic brace for a treatment area of a human body, the brace having a main panel, main panel fasteners at opposite ends of the main panel, and at least one reinforcing member cooperating with the main panel, the brace further having a ring-anchoring panel extending across the reinforcing member and securing two sliding rings to the main panel and at least two straps for applying compressive forces to the reinforcing member, the method comprising:
    a) encircling the treatment area with the brace;
    b) locating the at least one reinforcing member at the treatment area and fastening the brace using the main panel fasteners;
    c) adjusting the straps to apply compressive forces to the treatment area via the reinforcing member, wherein the step of adjusting further comprises threading the straps each through a respective one of the sliding rings, applying tension to the straps by pulling on the straps in opposite respective directions to apply force to the reinforcing member via the sliding rings, and fastening an end of each of the the straps to a respective one of the strap fastening pads;
    d) and maintaining compressive forces on the treatment area while undergoing activity.

16. The method of claim 15, wherein encircling the treatment area comprises encircling an area of a human leg above the ankle.

17. The method of claim 15, wherein locating the at least one reinforcing member at the treatment area comprises locating the at least one reinforcing member to apply pressure to the leg muscle just adjacent a human shin bone.

18. The method of claim 15, wherein the step of adjusting the straps comprises fastening the straps using hook-and-loop fasteners.

19. The method of claim 15, wherein the step of maintaining compressive forces comprises maintaining compressive forces on an area of the human leg above the ankle and adjacent the shin bone, and using the straps to maintain compressive forces on the human leg in a posterior location of the human leg.

20. An orthopedic brace for providing mobilization with movement therapy to a treatment area of the human body comprising:

a flexible main panel having two ends and including a main panel fastener for securing the ends of the main panel together and thereby securing the main panel in an encircling position around the treatment area;

a reinforcing member retaining panel attached to the main panel at a substantially central location thereof and forming a reinforcing member retaining pocket with the main panel;

the reinforcing member retaining panel further including at least one ring anchoring panel secured at opposite ends to the reinforcing member retaining panel and defining a ring anchoring area therewith, the ring anchoring area being located above the reinforcing member retaining pocket;

two sliding rings secured in the ring anchoring area such that the rings are permitted to move in a lateral direction relative to the main panel;

a reinforcing member disposed within the reinforcing member retaining pocket and extending beneath the ring anchoring panel;

at least two strap fastening pads comprising loop-type fasteners secured to the main panel at opposite sides thereof;

at least two straps, each having a first end fastened to the main panel at a position adjacent a respective strap fastening pad, and a second end having hook-type fasteners for engaging respective ones of the strap fastening pads, each strap adapted to extend through a respective one of the rings, such that tension applied to the second end of the strap pulls on the respective ring and results in an increased compressive force on the reinforcing member and the treatment area.

\* \* \* \* \*